(12) United States Patent
Bednarek

(10) Patent No.: US 6,960,646 B2
(45) Date of Patent: Nov. 1, 2005

(54) CYCLIC PEPTIDES AS POTENT AND SELECTIVE MELANOCORTIN-4 RECEPTORS AGONISTS

(75) Inventor: Maria A. Bednarek, Colonia, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/483,309

(22) PCT Filed: Jul. 8, 2002

(86) PCT No.: PCT/US02/21443

§ 371 (c)(1),
(2), (4) Date: Jan. 8, 2004

(87) PCT Pub. No.: WO03/006604

PCT Pub. Date: Jan. 23, 2003

(65) Prior Publication Data

US 2004/0171793 A1 Sep. 2, 2004

Related U.S. Application Data

(60) Provisional application No. 60/304,958, filed on Jul. 12, 2001.

(51) Int. Cl.[7] .................................................. C07K 7/50
(52) U.S. Cl. ..................... 530/317; 530/330; 514/11; 514/17; 514/18
(58) Field of Search ................................. 530/317, 330; 514/11, 17, 18

(56) References Cited

U.S. PATENT DOCUMENTS

2002/0143141 A1    10/2002    Li et al.

OTHER PUBLICATIONS

Arian Wai–Hing Cheung, et al., *Bioorganic & Medicinal Chemistry Letters*, 13, pp. 1307–1311, (2003).

Malcolm J. Kavarana, et al., *J. Med. Chem.*, 45, pp. 2644–2650, (2002).

Maria A. Bednarek, et al., *Biochemical and Biophysical Research Communications*, 286, pp. 641–645, (2001).

*Primary Examiner*—David Lukton
(74) *Attorney, Agent, or Firm*—Mollie M. Yang; David L. Rose

(57) ABSTRACT

Cyclic peptides of formula I are potent and selective agonists of melanocortin-4 receptors, and as such are useful research tool for the determination of the physiological roles of the MC-4 receptor, as well as for the diagnoses, treatment or prevention of disorders or diseases mediated through the MC-4 receptor.

10 Claims, No Drawings

CYCLIC PEPTIDES AS POTENT AND SELECTIVE MELANOCORTIN-4 RECEPTORS AGONISTS

CROSS REFERENCE TO RELATED APPLICATION

This application is the National Stage of International Application No. PCT/US02/21443, filed 8 Jul. 2002 which claims the benefit under 35 U.S.C. 119(e) of U.S. Provisional Application No. 60/304,958, filed 12 Jul. 2001.

BACKGROUND OF THE INVENTION

Melanocortin peptides or melanotropins, α-MSH, β-MSH, γ-MSH and ACTH, are involved in many physiological functions in vertebrates, mammals and in man. They regulate skin pigmentation and steroid production, modulate immune responses and learning processes, influence energy balance, growth and regeneration of nerves, and several other functions as well.

Five human receptors are known which interact with melanotropins, hMC-1R to hMC-5R. The receptors are seven-helix transmembrane-spanning receptors and belong to the superfamily of G protein-coupled receptors; their activation leads to elevation of cAMP. The melanocortin receptors 1, 3, 4 and 5 recognize α-MSH, β-MSH and γ-MSH, while melanocortin receptor 2 recognizes only ACTH.

Considerable attention has recently focused on melanocortin receptors 3 and 4 that are widely expressed in the central nervous system, and also on melanocortin receptor 5, found in the brain and in various peripheral tissues. The physiological role of hMC-3R and hMC-5R is not well defined, although hMC-5R has recently been implicated in control of lipid and pheromone production in exocrine glands. Rapidly growing pharmacological and genetic evidence suggests that hMC-4R is involved in regulation of the energy balance and body weight in rodents. The role of MC-4R in regulation of food intake and body weight is supported by results obtained from agonist/antagonist administration in rats and from murine genetics. Intraventricular administration of the agonist MTII reduced food intake and conversely, the antagonist SHU9119 increased food intake and body weight. Mice genetically deficient in the melanocortin receptor 4 develop obesity. It could be anticipated therefore that compounds active at MC-4R might be useful in the treatment of eating disorders.

Melanocortin receptor 4 appears to play a role in other physiological functions as well, namely in controlling grooming behavior, erection and blood pressure. The natural hormones, melanotropins, however, have relatively low affinity for hMC3-5R and are not particularly selective. In order to differentiate the physiological role of melanocortin receptor 4 from that of other melanocortin receptors in the brain, in particular from MC-3R, potent and selective antagonists are necessary. The synthetic ligands available at present do not distinguish between the melanocortin receptors. A frequently used research tool is the SHU9119 peptide, a potent antagonist at melanocortin receptors 3 and 4, and an agonist at melanocortin receptor 5. SHU9119 has been extensively studied in vitro and in vivo; injection of this peptide stimulates food intake in rats. A similar lactam derivative, the peptide MTII is a potent but non-selective agonist at hMC3-5R.

SUMMARY OF THE INVENTION

The present invention provides cyclic peptides that are potent and selective agonists of the human melanocortin-4 receptor. These compounds are useful as research tool for the determination of the physiological roles of the MC-4 receptor, as well as for the diagnosis, treatment or prevention of disorders or diseases mediated through the MC-4 receptor.

DETAILED DESCRIPTION OF THE INVENTION

The present invention provides compounds of the formula I

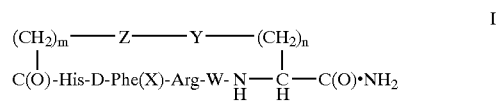

wherein,
His is L-histidyl;
D-Phe(X) is D-phenylalanyl optionally para-substituted with a group selected from F, Cl, Br, Me, OMe;
Arg is L-arginyl;
W is L-tryptophanyl or 2-naphthyl-L-alanyl;
one of Y and Z is —C(O)— and the other is —NH—;
m is 1 to 4;
n is 1 to 4, provided that n+m is 4 to 6; or
a salt thereof.

In one embodiment of formula I, Z is —C(O)— and Y is —NH—. In one subset thereof m is 2. In another subset thereof n is 2 to 4. In another subset thereof, D-Phe(X) is D-phenylalanyl optionally para-substituted with chlorine.

In another embodiment Y is —C(O)—and Z is —NH—. In one subset thereof n is 2. In another subset thereof m is 2 to 4. Another subset thereof provides compounds where W is L-trytophanyl and D-Phe(X) is D-phenylalanyl.

Compounds of the present invention are potent and selective agonists of the melanocortin-4 receptor, and as such are useful as analytical research tool for the study of the physiological roles of the melanocortin-4 receptor. In addition, compounds of the present invention are useful for the diagnosis, treatment and prevention of diseases and disorders that may benefit from the activation of the MC-4 receptor, in particular diseases and disorders related to eating disorders.

For analytical and diagnostic purposes the compounds of the present invention can be used in radioactive form, including radioactive labels. In particular the compounds of the invention may be manufactured so as to incorporate radioactive iodine or tritium, or any other suitable radio nuclide. Such a radioactively labeled compound can be used in radioligand binding for the the quantification of specific melanocortin receptors, for the analysis of dissociation constant ($K_i$s or $K_d$s) of drugs competing with specific subtypes of melanocortin receptors, and for the localization of MC-receptors in tissues and tissue sections e.g. by use of receptor autoradiographic techniques. Principles of radioligand binding and receptor autoradiography are well known in the art. As an alternative the compound may be labeled with any other type of label that allows detection of the substance, e.g. a fluorescent label or biotin, and the resulting compound be used for the similar purpose as the radioactively labeled compound.

The compounds of the invention can also be manufactured so as to incorporate a group that can be activated by light, in particular UV-light, the purpose with such activation being to obtain a compound useful for covalent labeling of MC-receptor by use of the photoaffinity labeling technique. Photoaffinity labeling is a technique well known in the art which in the present context is useful for elucidating the structure and topological organisation of the MC-receptors. Thus photoactive derivatives of the compounds of the invention are also part of the present invention. Moreover, preferably photoactive derivates of the compounds of the invention may also be made to incorporate an easily detectable group or label, such as e.g. a radioactive atom, a fluorescent group and/or biotin.

The compounds of the invention can be labeled with gamma and/or positron emitting isotope(s). Such labeled compounds constitute very specific embodiments of the invention and may be administered systematically, or locally, to an animal, preferably a human. These labeled compounds are useful for imaging the in vivo levels and/or localization of MC-receptors by the use of well known techniques among which may be mentioned Scintigraphy, Positron Emission Tomography (PET) and Single Photon Emission Computed Tomography (SPECT). Using such methods information on the distribution and/or quantities of the specific MC-receptors in tissues of the animal or human subject to the investigation is obtained, and such information is of value for diagnosis of disease, in particular functional disturbances in the brain related to MC-receptors.

In addition to analytical and diagnostic utilities, peptides of the present invention may also be used to activate the normal physiological response of cells to natural melanotropin (e.g., .alpha.-MSH) at the MC-4 receptor. Accordingly, compounds of formula I are useful in the treatment, control or prevention of diseases, disorders or conditions responsive to the activation MC-4 receptor such as the prevention and treatment of obesity, as well as male and female sexual dysfunction.

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Pharmacologically effective amounts may vary from 0.001 mg/day/kg body weight to 1,000 mg/day/kg body weight. Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. The effective dosage of active ingredient employed may vary depending on the particular compound employed, the mode of administration, the condition being treated and the severity of the condition being treated. Such dosage may be ascertained readily by a person skilled in the art.

The following examples are provided to illustrate the present invention is not to be construed as limiting the invention in any manner.

EXAMPLES 1–9
Synthesis of Cyclic Peptides

Elongation of peptidyl chains on p-methoxybenzhydrylamine resin was performed on a 431A ABI peptide synthesizer. Manufacturer-supplied protocols were applied for coupling of the hydroxybenzotriazole esters of amino acids in N-methylpyrrolidone (NMP). The tert-butyloxycarbonyl (Boc) group was used as a semi-permanent alpha-amino protecting group, whereas the side chain protecting groups were: tosyl for arginine, benzyloxymethyl for histidine, fluorenylmethyloxycarbonyl (Fmoc) for lysine, and fluorenylmethyl (Fm) for aspartic acid. Chain building on the synthesizer was concluded by acetylation of the N-terminal residue. The peptidyl resin was transferred into a vessel and Fmoc and Fm groups were manually removed with 20% piperidine in NMP (20 minutes at room temperature).

For cyclization, the peptidyl resin was thoroughly washed, and then agitated overnight with 5-fold excess of benzotriazole-1-yl-oxy-tris-pyrrolidino-phosphonium hexafluorophosphate (PyBoc) and 6-fold excess of diisopropylethylamine in NMP. The procedure was repeated until a negative Kaiser test was observed. The peptidyl resin was washed with NMP and methanol, dried, and treated with liquid hydrogen fluoride in the presence of anisole (or p-cresol) as scavenger (9:1, v/v). After 1 hour at 0° C., hydrogen fluoride was removed in vacuo, the resin was washed with ether and extracted with glacial acetic acid, and the extract was lyophylized. The crude peptide was analyzed by analytical reverse-phase high-pressure liquid chromatography (RP HPLC) on a C18 Vydac column attached to a Waters 600E system with authomatic Wisp 712 injector and 991 Photodiode Array detector. A standard gradient system of 0–100% buffer B in 30 minutes (G1), and, a gradient of 20–80% buffer B in 30 minutes (G2) was used for analysis: buffer A was 0.1% trifluoroacetic acid in water and buffer B was 0.1% triflouroacetic acid in acetonitrile. HPLC profiles were recorded at 210 nm and 280 nm. Preparative separations were performed on a Waters Delata Prep 40000 system with a semipreparative C18 RP Waters column. The above-described solvent system of water and acetonitrile, in a gradient of 20–80% buffer B in 60 minutes (G3) was used for separation.

For several compounds, the peptidyl resin was transferred into a vessel, agitated with 6-fold excess of succinic anhydride and 6-fold excess of diisopropylethylamine in N-methylpyrrolidone until a negative Kaiser test was observed, and then thoroughly washed with N-methylpyrrolidone and methanol. Subsequent removal of Fmoc group, cyclization, deprotection and cleavage of peptides from a resin, and purification of the crude products were performed as described above.

The chromatographically homogenous compounds were analyzed by amino acid analysis and electrospray mass spectrometry. Correct mass was identified by electrospray mass spectrometry (Hewlett Packard series 1100 MSD spectrometer). Examples of compounds prepared in accordance with the above general procedure are shown in the following Table.

$$(CH_2)_m\text{------}Z\text{------}Y\text{------}(CH_2)_n$$
$$|\qquad\qquad\qquad\qquad\qquad|$$
$$C(O)\text{-His-D-Phe}(X)\text{-Arg-W-}\underset{H}{N}\text{---}\underset{H}{C}\text{---}C(O)\cdot NH_2$$

| Example | Z | Y | X | W | m | N |
|---|---|---|---|---|---|---|
| 1 | C(O) | NH | H | Trp | 2 | 4 |
| 2 | C(O) | NH | H | Trp | 2 | 2 |
| 3 | C(O) | NH | H | Trp | 2 | 1 |
| 4 | C(O) | NH | Para-Cl | Trp | 2 | 4 |
| 5 | C(O) | NH | H | 2-Nal | 2 | 4 |
| 6 | NH | C(O) | H | Trp | 4 | 2 |
| 7 | NH | C(O) | H | Trp | 3 | 2 |
| 8 | NH | C(O) | H | Trp | 2 | 2 |
| 9 | NH | C(O) | H | Trp | 1 | 2 |

EXAMPLE 10
Competitive Binding Assay

The peptides of the present invention were evaluated for agonist activity in receptor binding assay. Crude membrane preparations were obtained from Chinese hamster ovary cells expressing human MC3, MC4, and MC5 receptors. Cells were rinsed with phosphate-buffered saline (PBS) lacking $CaCl_2$ or $MgCl_2$ (Life Technologies, Gaithersburg, Md., USA), and then detached with enzyme-free dissociation media (Specialty Media, Lavellette, N.J., USA). Cells were pelleted at 2800×g for 10 minutes and resuspended in membrane buffer (20 mM Tris, pH 7.2, 5 mM ethylenediaminetetraacetic acid) with 5 µg/ml leupeptin, 5 µg/ml aprotinin, 40 µg/ml bacitracin, and 25 µg/ml pefabloc (Boehringer Mannheim). The cells were doused with 10 strokes by using a motor-driven Teflon-coated pestle in a glass homogenizer at low speed. The resulting cell suspension was centrifuged at 4100×g, 4° C., for 20 minutes. The pellet was resuspended in fresh membrane buffer with protease inhibitors, aliquoted, snap-frozen in liquid nitrogen, and stored at −80° C. The resulting crude membranes were titrated to determine the optimal level necessary for performing binding studies.

Binding reactions (total volume=250 µl) contained MBB (50 mM Tris, pH 7.2, 2 mM $CaCl_2$, 1 mM $MgCl_2$), 0.1% bovine serum albumin, crude membranes prepared from cells expressing human MC3, MC4, or MC5 receptor, 200 pM of [125I]-NDP-α-MSH (Amersham, Arlington Heighs, Ill., USA), and increasing concentrations of unlabeled test compounds dissolved in dimethylsulfoxide (final concentration=2%). Reactions were incubated for 1 hour without shaking and then filtered through 96-well filter plates (Packard), presoaked in 1% polyethyleneimine. Filters were washed 3 times with TNE buffer (50 mM Tris, pH 7.4, 5 mM ethylene-diaminetetraacetic acid, 150 mM NaCl), dried and counted by using Microscint-20 in a Topcount scintillation counter (Packard). Nonspecific binding was determined in the presence of 2 µm of unlabeled NDP-α-MSH (Peninsula Laboratories). Binding data were analyzed with GraphPad curve-fitting software (PRISM, San Diego, Calif.) and are presented in the Table below. Active peptides were evaluated in three independent experiments.

EXAMPLE 11
cAMP Assays

Chinese hamster ovary cells expressing a human melanocortin receptor were rinsed with calcium- and magnesium-free PBS (Life Technologies), and detached from the tissue culture flasks by 5-minutes incubation with enzyme-free dissociation buffer (S-014-B, Specialty Media). Cells were collected by centrifugation and resuspended in Earle's balanced salt solution (Life Technologies) with addition of 10 mM 4-(2-hydroxyethyl)-1-piperazineethanesulfonic acid (Hepes) buffer, pH 7.5, 5 mM MgCl2, 1 mM glutamine, and 1 mg/ml bovine serum albumin to concentration of $1-5\times10^6$ cells/ml. Subsequently, cells were counted and the cell suspension was treated with the phosphodiesterase inhibitor 3-isobutyl-1-methylxanthine (to concentration of 0.6 mM).

A test compound was dissolved in dimethyl sulfoxide (DMSO, $10^{-3}$ to $10^{-8}$ M), diluted with buffer, and 0.1 volume of the solution was added to 0.9 volumes of the cell suspension (1 to $5\times10^5$ cells); final concentration of DMSO was 1%. After 45 minutes at room temperature, cells were lysed by incubation at 100° C. for 5 minutes to release accumulated cAMP. Accumulation of cAMP was measured in an aliquot of the cell lysate with the Amersham (Arlington Heights, Ill.) cAMP detection assay kit (RPA556). The amount of cAMP produced in response to a tested compound was compared to the amount of cAMP produced in response to α-MSH, defined as a 100% agonist. All active peptides were characterized in three independent experiments.

Results of binding assay and cAMP assay (Examples 10 and 11, respectively) for representative compounds of the present invention are provided below:

| | Binding Assay $IC_{50}$ (nM) | | CAMP Assay $EC_{50}$ (nM) | | |
|---|---|---|---|---|---|
| Ex | hMC-3R | hMC-4R | hMC-5R | hMC-3R | hMC-4R | hMC-5R |
| 1 | 418 | 25 | 3103 | 110 | 3.3 | 1180 |
| 2 | 1800 | 35 | 7200 | 240 | 2.9 | 2200 |
| 3 | 1600 | 71 | 3600 | 590 | 33 | 12% @ 5 |
| 4 | 17 | 1.7 | 92 | 40 | 0.74 | 170 |
| 5 | 440 | 13 | >20000 | 360 | 3.7 | >5000 |
| 6 | 580 | 12 | 9000 | 190 | 2.7 | 1900 |
| 7 | 1830 | 41 | >5000 | 310 | 5.7 | >5000 |
| 8 | 450 | 4 | 5050 | 59 | 0.53 | 1900 |
| 9 | >1000 | 290 | >1000 | 2200 | 35 | 15% @ 5 |

What is claimed is:

1. A compound having the formula I:

$$\begin{array}{c} (CH_2)_m\text{——}Z\text{——}Y\text{——}(CH_2)_n \\ | \quad\quad\quad\quad\quad\quad\quad\quad\quad | \\ C(O)\text{-His-D-Phe(X)-Arg-W-}\underset{H}{N}\text{——}\underset{H}{C}\text{——}C(O)\cdot NH_2 \end{array}$$

I wherein,

His is L-histidyl;

D-Phe(X) is D-phenylalanyl optionally para-substituted with a group selected from F, Cl, Br, Me, OMe;

Arg is L-arginyl;

W is L-tryptophanyl or 2-naphthyl-L-alanyl;

one of Y and Z is —C(O)— and the other is —NH—;

m is 1 to 4;

n is 1 to 4, provided that n+m is 4 to 6; or a salt thereof.

2. A compound of claim 1 wherein Z is —C(O)— and Y is —NH—.

3. A compound of claim 2 wherein m is 2.

4. A compound of claim 2 wherein n is 2 to 3.

5. A compound of claim 2 wherein m is 2 and n is 2.

6. A compound of claim 2 wherein D-Phe(X) is D-phenylalanyl optionally parasubstituted with chlorine.

7. A compound of claim 1 wherein Y is —C(O)— and Z is —NH—.

8. A compound of claim 7 wherein m is 2 and n is 2.

9. A compound of claim 1 selected from:

$$\begin{array}{c} (CH_2)_m\text{——}Z\text{——}Y\text{——}(CH_2)_n \\ | \quad\quad\quad\quad\quad\quad\quad\quad\quad | \\ C(O)\text{-His-D-Phe(X)-Arg-W-}\underset{H}{N}\text{——}\underset{H}{C}\text{——}C(O)\cdot NH_2 \end{array}$$

| Z | Y | X | W | m | N |
|---|---|---|---|---|---|
| C(O) | NH | H | Trp | 2 | 4 |
| C(O) | NH | H | Trp | 2 | 2 |
| C(O) | NH | H | Trp | 2 | 1 |
| C(O) | NH | Para-Cl | Trp | 2 | 4 |
| C(O) | NH | H | 2-Nal | 2 | 4. |

10. A compound of claim 1 selected from:

$$\begin{array}{c} (CH_2)_m\text{——}Z\text{——}Y\text{——}(CH_2)_n \\ | \quad\quad\quad\quad\quad\quad\quad\quad\quad | \\ C(O)\text{-His-D-Phe(X)-Arg-W-}\underset{H}{N}\text{——}\underset{H}{C}\text{——}C(O)\cdot NH_2 \end{array}$$

| Z | Y | X | W | m | N |
|---|---|---|---|---|---|
| NH | C(O) | H | Trp | 4 | 2 |
| NH | C(O) | H | Trp | 3 | 2 |
| NH | C(O) | H | Trp | 2 | 2 |
| NH | C(O) | H | Trp | 1 | 2. |

* * * * *